(12) United States Patent
Vorwerk et al.

(10) Patent No.: US 11,660,361 B2
(45) Date of Patent: May 30, 2023

(54) METHOD AND DEVICE FOR THE PLASMA PROCESSING OF CONTAINERS

(71) Applicant: KHS GMBH, Dortmund (DE)

(72) Inventors: Juergen Franz Vorwerk, Moersdorf (DE); Igor Singur, Bad Kreuznach (DE); Sebastian Kytzia, Todesfelde (DE)

(73) Assignee: KHS GmbH, Dortmund (DE)

( * ) Notice: Subject to any disclaimer, the term of this patent is extended or adjusted under 35 U.S.C. 154(b) by 622 days.

(21) Appl. No.: 16/062,018

(22) PCT Filed: Nov. 24, 2016

(86) PCT No.: PCT/EP2016/078731
§ 371 (c)(1),
(2) Date: Oct. 10, 2018

(87) PCT Pub. No.: WO2017/102280
PCT Pub. Date: Jun. 22, 2017

(65) Prior Publication Data
US 2019/0076560 A1 Mar. 14, 2019

(30) Foreign Application Priority Data
Dec. 14, 2015 (DE) .................. 102015121773.2

(51) Int. Cl.
*A61L 2/14* (2006.01)
*A61L 2/20* (2006.01)
(Continued)

(52) U.S. Cl.
CPC .............. *A61L 2/14* (2013.01); *A61L 2/202* (2013.01); *A61L 2/208* (2013.01); *C23C 16/045* (2013.01);
(Continued)

(58) Field of Classification Search
CPC ............ A61L 2/14; A61L 2/202; A61L 2/208; A61L 2202/23; C23C 16/54;
(Continued)

(56) References Cited

U.S. PATENT DOCUMENTS 6,276,296 B1  8/2001  Plester
6,403,029 B1  6/2002  Schmidt
(Continued)

FOREIGN PATENT DOCUMENTS

DE   19944631 A1   3/2001
DE   10114401 A1   9/2002
(Continued)

OTHER PUBLICATIONS

WO2017/0102280A3—International Search Report, dated Nov. 13, 2017.
(Continued)

*Primary Examiner* — Regina M Yoo
(74) *Attorney, Agent, or Firm* — Rankin, Hill & Clark LLP

(57) ABSTRACT

The invention relates to a method and an apparatus for the plasma treatment of containers. The essential aspect according to the method according to the invention is that, after the plasma treatment at the plasma station and before the container is filled, at least the container interior of the container is at least partially ventilated with a sterilization medium, i.e. is loaded with a sterilization medium.

9 Claims, 6 Drawing Sheets

(51) Int. Cl.
  *C23C 16/04* (2006.01)
  *C23C 16/54* (2006.01)
  *C23C 16/44* (2006.01)
  *C23C 16/52* (2006.01)
  *H01J 37/32* (2006.01)

(52) U.S. Cl.
  CPC ......... *C23C 16/4409* (2013.01); *C23C 16/52* (2013.01); *C23C 16/54* (2013.01); *H01J 37/32201* (2013.01); *A61L 2202/23* (2013.01)

(58) Field of Classification Search
  CPC ............... C23C 16/4409; C23C 16/52; C23C 16/045; H01J 37/32201
  See application file for complete search history.

(56) References Cited

U.S. PATENT DOCUMENTS

| | | | |
|---|---|---|---|
| 8,268,257 B2 | 9/2012 | Frost | |
| 8,372,491 B2 | 2/2013 | Rostaing | |
| 8,746,172 B2 | 6/2014 | Krueger et al. | |
| 8,790,589 B2* | 7/2014 | Cirri | B65B 55/08 422/292 |
| 2001/0042510 A1 | 11/2001 | Plester | |
| 2006/0150909 A1 | 7/2006 | Behle | |
| 2008/0035059 A1 | 2/2008 | Wang et al. | |
| 2009/0304950 A1 | 12/2009 | Rostaing | |
| 2011/0186537 A1* | 8/2011 | Rodriguez San Juan | B05D 1/60 215/355 |
| 2012/0017783 A1* | 1/2012 | Uptergrove | B41F 17/18 101/38.1 |
| 2013/0186336 A1 | 7/2013 | Siebels et al. | |
| 2014/0004022 A1* | 1/2014 | Sagona | C23C 16/54 422/558 |
| 2014/0102639 A1 | 4/2014 | Nettesheim et al. | |
| 2014/0311095 A1 | 10/2014 | Hayakawa et al. | |
| 2015/0079309 A1 | 3/2015 | Krueger et al. | |
| 2015/0098084 A1* | 4/2015 | Felts | G01N 15/082 356/432 |
| 2015/0183540 A1 | 7/2015 | Lothas | |

FOREIGN PATENT DOCUMENTS

| | | |
|---|---|---|
| DE | 10224395 A1 | 12/2003 |
| DE | 10225609 A1 | 12/2003 |
| DE | 102008016923 A1 | 10/2009 |
| EP | 2151510 A1 | 2/2010 |
| EP | 2772447 A1 | 9/2014 |
| EP | 3199489 A1 | 8/2017 |
| JP | H08509166 A | 10/1996 |
| JP | 2005081309 A | 3/2005 |
| JP | 2007313309 A | 12/2007 |
| JP | 2009545673 A | 12/2009 |
| JP | 2014526116 A | 10/2014 |
| WO | 0000394 A1 | 1/2000 |
| WO | 20080083824 A2 | 7/2008 |
| WO | 20110153993 A1 | 12/2011 |
| WO | 20130061956 A1 | 5/2013 |

OTHER PUBLICATIONS

German PTO's Examination Report dated Feb. 20, 2019, issued for the German priority application No. DE 10 2015121773.2, filed Dec. 14, 2015.
Notice of Reasons for Refusal issued in Corresponding JP Application No. 2018-530567 dated May 27, 2020 (Japanese and English translation).
International Search Report issued in corresponding International Application No. PCT/EP2016/078731 dated Nov. 23, 2017.
European Office Action issued in corresponding European Application No. 16 802 023.8 dated Jun. 8, 2020.

* cited by examiner

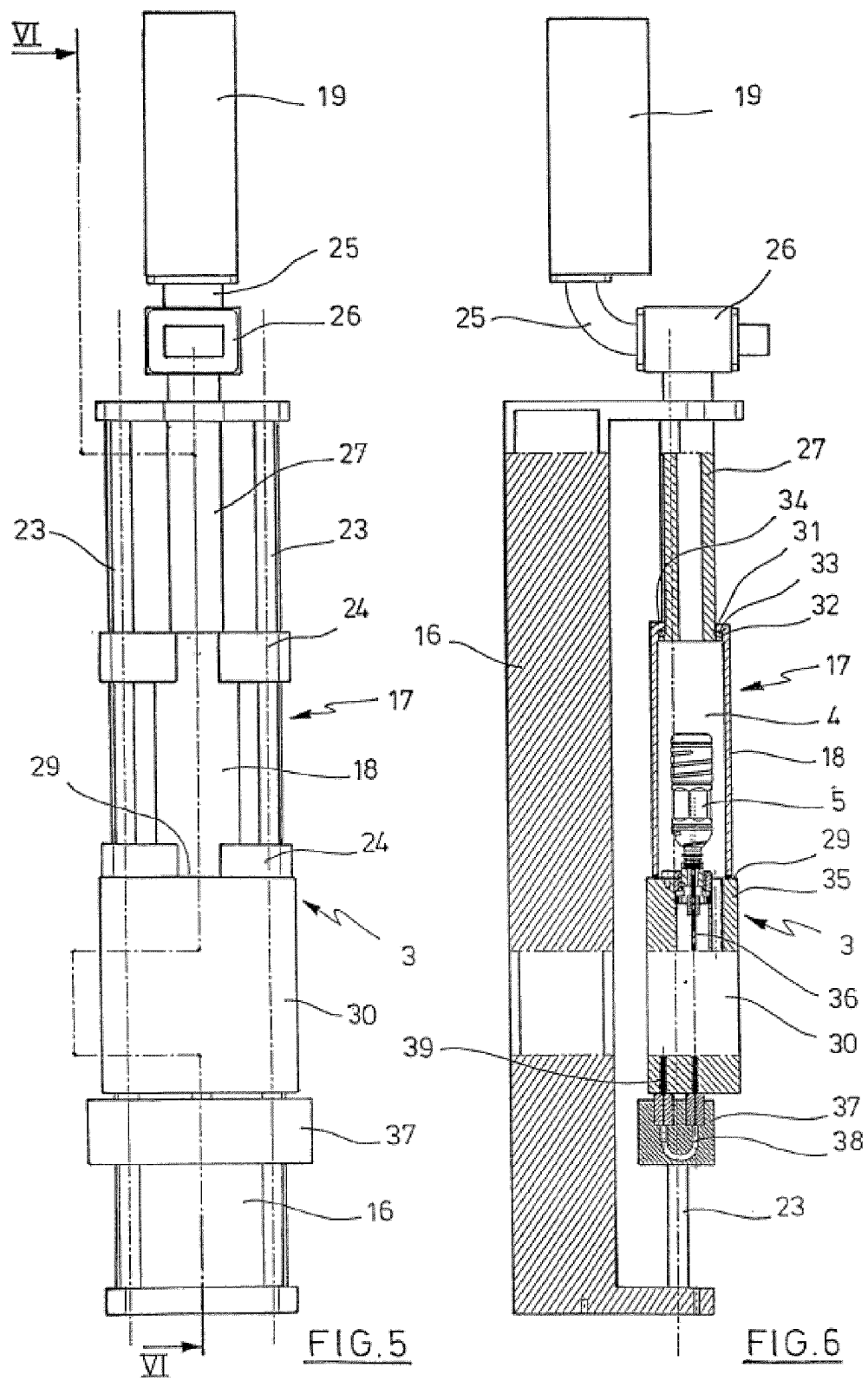

METHOD AND DEVICE FOR THE PLASMA PROCESSING OF CONTAINERS

CROSS-REFERENCES TO RELATED APPLICATIONS

This application claims the benefit under 35 U.S.C. § 371 to international application No. PCT/EP2016/078731, filed on Nov. 24 3, 2016, which claims priority to German patent application No. 102015121773.2, filed Dec. 14, 2015, the contents of which are incorporated by reference herein in their entireties.

FIELD OF THE INVENTION

The invention relates to a method for the plasma treatment of containers. The invention furthermore relates to an apparatus for the plasma treatment of containers.

BACKGROUND OF THE INVENTION

Such methods and apparatuses are used, for example, to provide plastics with surface coatings. In particular, such apparatuses are also already known in order to coat internal or external surfaces of containers which are intended for the packaging of liquids. In addition, devices for plasma sterilization are known.

A plasma chamber for the internal coating of containers made of PET is described in the published document WO95/22413 A1. The containers to be coated are raised into a plasma chamber by a movable base and brought into connection with an adapter in the area of a container opening. The container interior can be evacuated through the adapter. In addition, a hollow gas lance is inserted through the adapter into the interior of the containers in order to feed in process gas. The plasma is ignited using a microwave.

It is also already known from this publication to arrange a plurality of plasma chambers on a rotating wheel. A high production rate of containers per unit of time is supported hereby.

Published document EP 10 10 773 A1 gives an explanation of a feed device in order to evacuate a bottle interior and supply it with process gas. WO 01/31680 A1 describes a plasma chamber into which the bottles are introduced by a movable cover which has previously been connected to an opening area of the bottles.

Published document WO 00/58631 A1 likewise already shows the arrangement of plasma stations on a rotating wheel and describes, for such an arrangement, a grouped allocation of vacuum pumps and plasma stations in order to support a favourable evacuation of the chambers as well as the interiors of the bottles. In addition, the coating of several containers in a common plasma station or a common cavity is mentioned.

A further arrangement for carrying out an internal coating of bottles is described in the published document WO 99/17334 A1. Here, in particular, an arrangement of a microwave generator above the plasma chamber as well as a vacuum and operating fluid feed line through a base of the plasma chamber is described.

DE 10 2004 020 185 A1 already describes a gas lance which can be moved into the interior of a preform to be coated and serves to feed in process gases. The gas lance can be positioned in the longitudinal direction of the container.

In most of the known apparatuses, plasma-produced container layers of silicon oxides with the general chemical formula SiOx are used to improve barrier properties of the thermoplastic plastic material. Such barrier layers, in particular on the internal wall of a container interior, prevent oxygen from penetrating into the packaged liquids as well as preventing carbon dioxide from escaping in the case of $CO_2$-containing liquids, and thus improve the storage properties or the lasting stability of the liquids poured into and/or packaged in the container.

The object of the invention is to specify a method and an apparatus for the plasma treatment of containers, in which the storage properties of the container interior are further improved compared with the state of the art. To achieve this object, a method for the plasma treatment of workpieces and apparatus for the plasma treatment of containers is disclosed herein.

SUMMARY OF THE INVENTION

The essential aspect according to the method according to the invention is that, after the plasma treatment and before the filling of the container in the plasma chamber, at least the container interior of the at least one container is loaded with a sterilization medium in the form of gas, vapour or mist, namely preferably such that during the ventilation step at least the container interior is at least partially ventilated with the sterilization medium in the form of gas, vapour or mist. The state of aggregation of the above-named sterilization medium relates to atmospheric pressure or to the state of aggregation of the fluid in the corresponding feed line.

Particularly advantageously, differing from the state of the art, the evacuated plasma chamber including the container located therein is thus not ventilated at ambient pressure, as was previously usual in the state of the art, but a sterilization medium is introduced in a targeted manner via the ventilation thereof, in order thus to create a sterilizing atmosphere inside the container interior for the later filling process already at the end of the plasma treatment, and thus in particular still on the plasma module. Suitable in particular as sterilization medium is a sterilization medium containing hydrogen peroxide ($H_2O_2$) which is used, for example, together with hot sterile air and thus condenses on the colder container interior as an $H_2O_2$ condensate film.

The ventilation of the container interior with sterilization medium can be particularly advantageously effected such that during the ventilation step a sterilization medium is introduced at least once into the container interior. The sterilization medium can thus be introduced into at least the container interior of the container particularly advantageously via the ventilation step. By ventilation or the ventilation step is meant the introduction of a fluid, in particular comprising or consisting of a gas or gas mixture for the purpose of raising the vacuum or the negative pressure in an evacuated chamber and/or in a container interior.

The ventilation can advantageously be effected by means of the sterilization medium at the plasma station of a plasma wheel, wherein at least one subsequent treatment can be effected in the area of an output wheel or the transition section to the next treatment machine. Furthermore advantageously, the container interior of the container can be loaded with the sterilization medium at least up to atmospheric pressure or above, i.e. a positive pressure. It can preferably be provided that the loading of at least the container interior of the container is effected with a sterilization medium containing hydrogen peroxide and/or ozone.

In an advantageous embodiment variant, in addition to the container interior of the container, the plasma chamber, and thus also the container's external surface, can also be at least partially ventilated with the sterilization medium.

It can also particularly preferably be provided that a subsequent activation and/or drying of the sterilization medium is effected. Activation and drying devices suitable for this are correspondingly known to a person skilled in the art. At least the activation of the sterilization medium for the respective container can advantageously be effected in the area of the output wheel. Alternatively the activation of the respective container can also advantageously be effected during its transport to a container treatment machine downstream of a plasma module. In a preferred embodiment variant, it can also be provided that the drying of the respective container is effected during its transport to a container treatment machine downstream of a plasma module.

In a preferred embodiment variant, before a repeated plasma treatment, at least one first to third process gas line as well as a central process gas line can be evacuated by suction and/or rinsed.

The ventilation by means of sterilization medium can advantageously be effected at least via a second ventilation line, opening in a fluid-tight manner into the central process gas line, which is formed so that it can be switched on and/or off controlled and/or regulated via a valve device.

The ventilation by means of sterilization medium can advantageously also be effected via a further first ventilation line, opening in a fluid-tight manner into a second side of a vacuum channel, which is formed so that it can be switched on and/or off controlled and/or regulated via a valve device (76.1).

Again advantageously, the ventilation by means of sterilization medium can be effected via yet another, third ventilation line, opening in a fluid-tight manner into the plasma chamber, which is formed so that it can be switched on and/or off controlled and/or regulated via a valve device.

In an advantageous embodiment, an additional blocking valve device, ideally a three-way valve, is provided in a fluid connection between the central vacuum device. This blocking device makes it possible for there to be a spatial delimitation of the lines at least at times during the ventilation with a sterilization agent, by closing this blocking device at times as needed. A contamination of at least one of the vacuum lines, a group of vacuum lines or partial sections of one or more vacuum lines with sterilization medium is thus securely prevented, or limited as far as possible.

By "container" is meant within the framework of the invention, in particular, cans, bottles, barrels, also kegs, tubes, pouches, in each case made of metal, glass and/or plastic, but also other packaging means, in particular also those which are suitable to be filled with powdered, granulated, liquid or viscous products.

The expression "substantially" or "approximately" or "approx." within the meaning of the invention means deviations from the exact value in each case by +/−10%, preferably by +/−5% and/or deviations in the form of changes that are insignificant with respect to function.

Developments, advantages and possible applications of the invention are also revealed by the following description of embodiment examples and by the figures. All features described and/or represented visually are in principle a subject of the invention individually or in any combination, independently of their summarization in the claims or references back. The content of the claims is also made a constituent of the description.

BRIEF DESCRIPTION OF THE DRAWINGS

The invention is explained in more detail below using embodiment examples with reference to the figures. There are shown in.

DETAILED DESCRIPTION OF THE EMBODIMENTS

Figure 1:
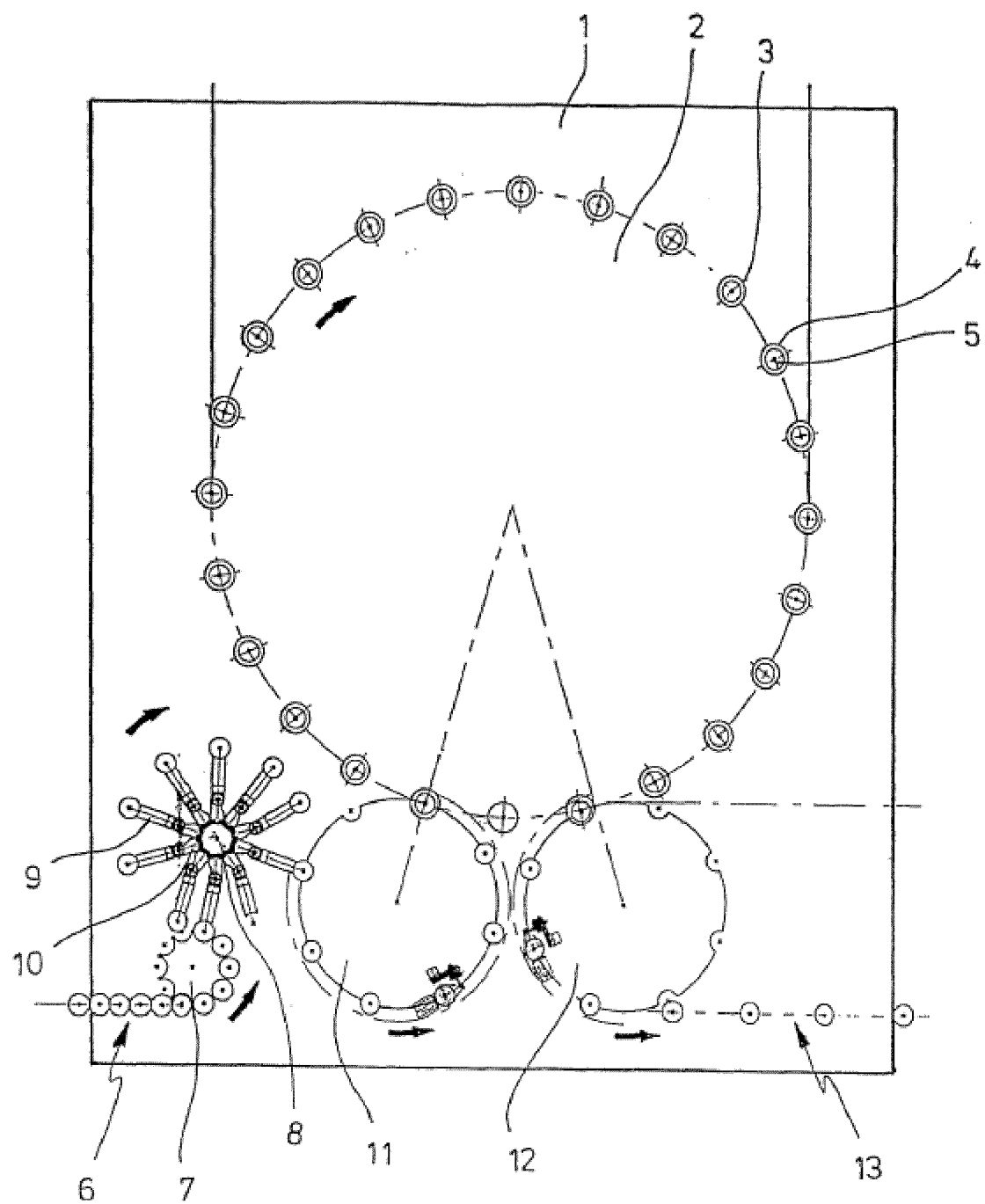
FIG. 1 a schematic diagram of a plurality of plasma chambers which are arranged on a rotating plasma wheel and in which the plasma wheel is coupled to input and output wheels, FIG. 2 an arrangement according to FIG. 1, in which the plasma stations each have two plasma chambers, FIG. 3 a perspective representation of a plasma wheel with a plurality of plasma chambers, FIG. 4 a perspective representation of a plasma station with a cavity, FIG. 5 a front view of the apparatus according to FIG. 4 with closed plasma chamber, FIG. 6 a cross section along section line VI-VI in FIG. 5, FIG. 7 a schematic block diagram of a plasma station formed according to the invention.

In FIG. 1, reference number 1 generally denotes a plasma module which is provided with a rotating plasma wheel 2. A plurality of plasma stations 3 are arranged along a circumference of the plasma wheel 2. The plasma stations 3 are provided with cavities 4 or plasma chambers 17 for accommodating containers 5 to be processed, each with at least one container interior 5.1.

The containers 5 to be treated are fed to the plasma module 1 in the area of an input 6 and transferred to a delivery wheel 8, which is equipped with positionable supporting arms 9, via a separating wheel 7. The supporting arms 9 are arranged pivotably relative to a pedestal 10 of the delivery wheel 8, with the result that a change in the spacing of the containers 5 relative to each other can be carried out. The containers 5 are hereby delivered by the delivery wheel 8 to an input wheel 11 with a spacing of the containers 5 relative to each other that has been increased relative to the separating wheel 7. The input wheel 11 delivers the containers 5 to be treated to the plasma wheel 2. After the treatment has been carried out, the treated containers 5 are removed from the area of the plasma wheel 2 by an output wheel 12 and transferred into the area of an output section 13.

Figure 2:
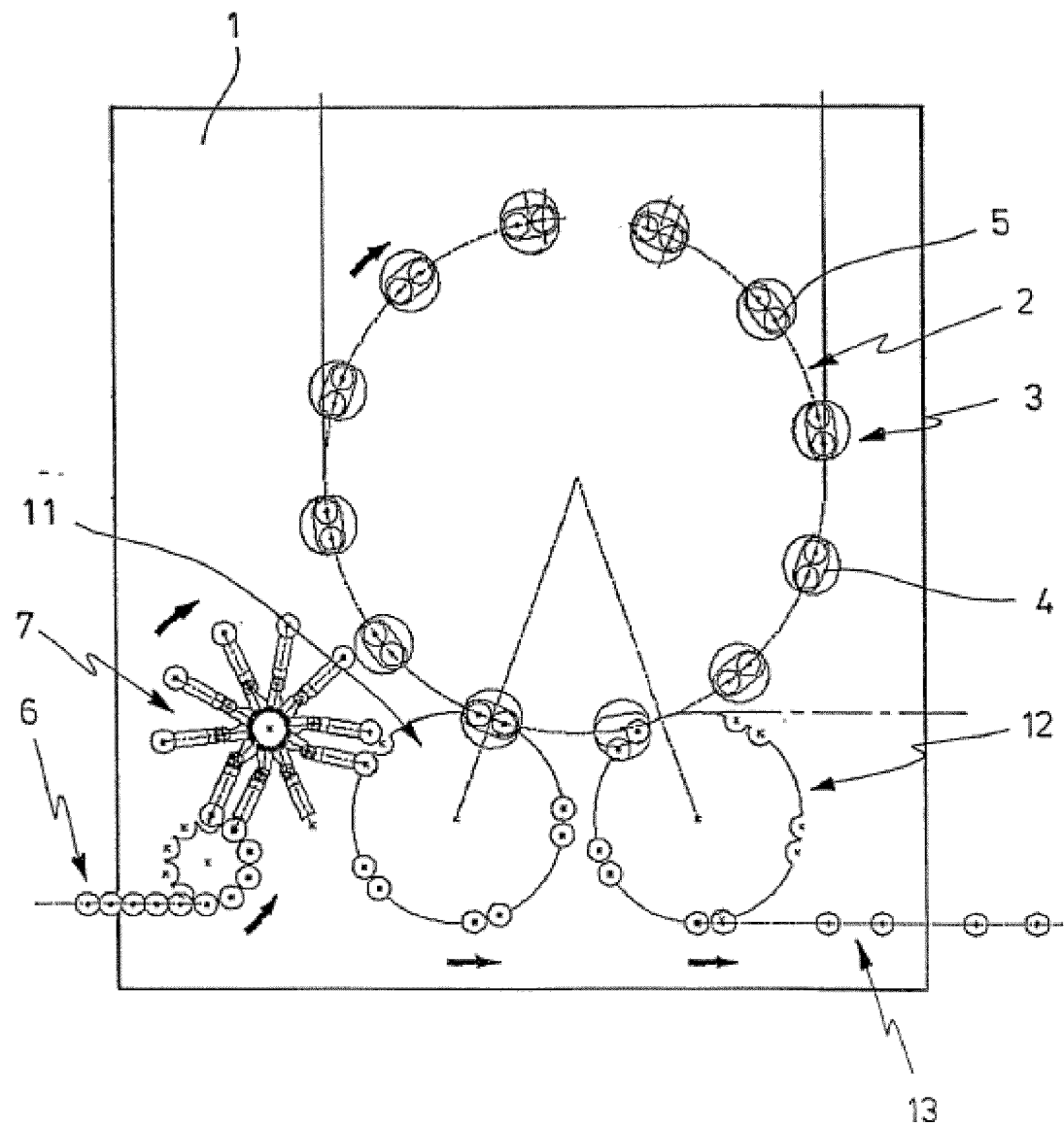

In the embodiment according to FIG. 2 the plasma stations 3 are each equipped with two cavities 4 or plasma chambers 17. In each case two containers 5 can hereby be treated at the same time. In principle it is possible here to form the cavities 4 completely separate from each other, but it is also possible in principle merely to delimit partial areas in a common cavity space such that an optimum coating of all containers 5 is guaranteed. It is considered in particular here to delimit the partial cavities in relation to each other at least by separate microwave couplings.

Figure 3:
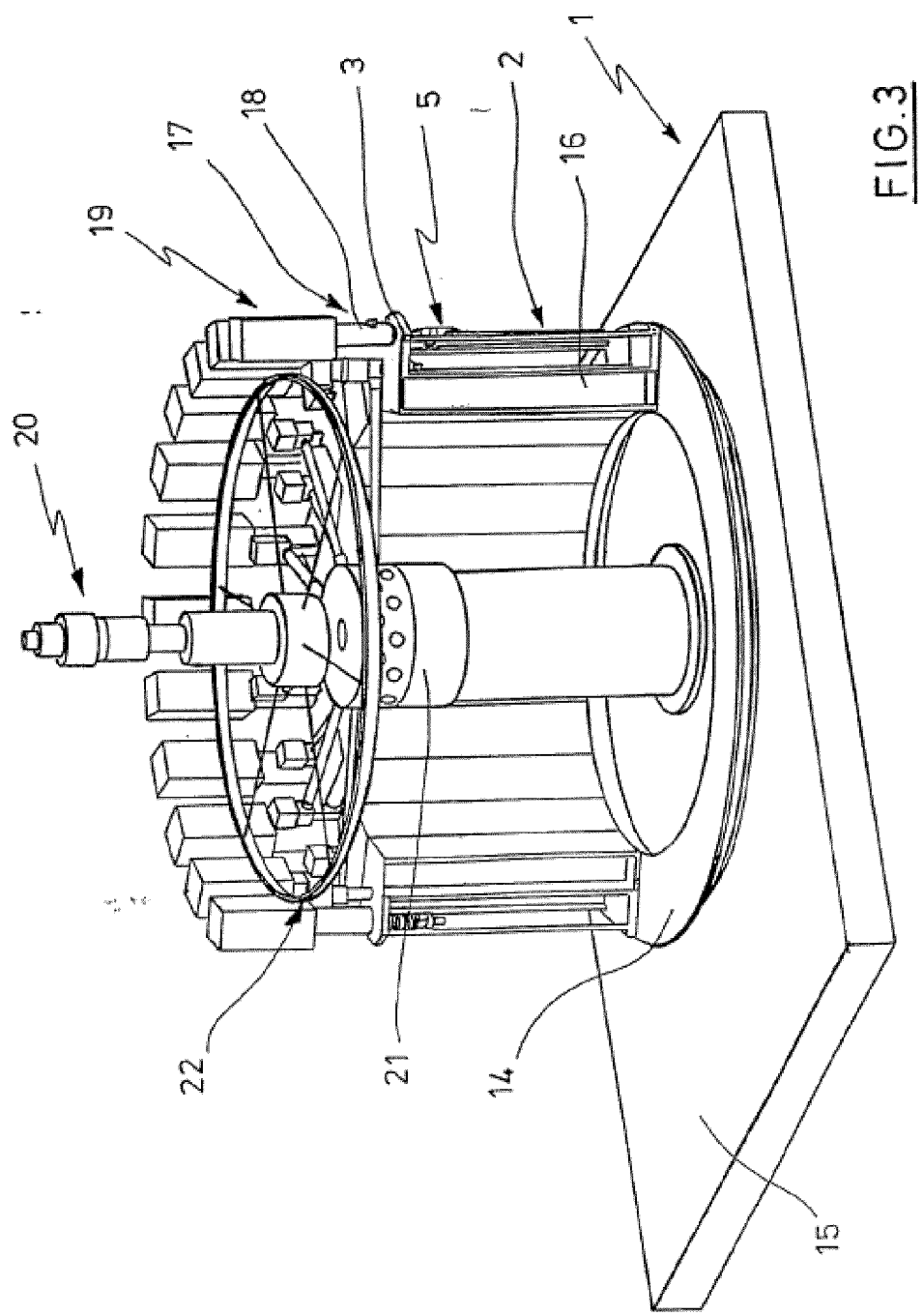

FIG. 3 shows a perspective representation of a plasma module 1 with partially assembled plasma wheel 2. The plasma stations 3 are arranged on a supporting ring 14, which is formed as part of a rotary joint and mounted in the area of a machine pedestal 15. The plasma stations 3 each have a station frame 16, which holds the plasma chambers 17. The plasma chambers 17 can have cylindrical chamber walls 18 as well as microwave generators 19.

In a centre of the plasma wheel 2, a rotary distributor 20 can be provided, via which the plasma stations 3 are supplied with operating fluid as well as energy. In particular, ring lines 21 can be used to distribute operating fluid.

The containers 5 to be treated are represented underneath the cylindrical chamber walls 18, wherein for simplification in each case lower parts of the plasma chambers 17 are not drawn in.

Figure 4:
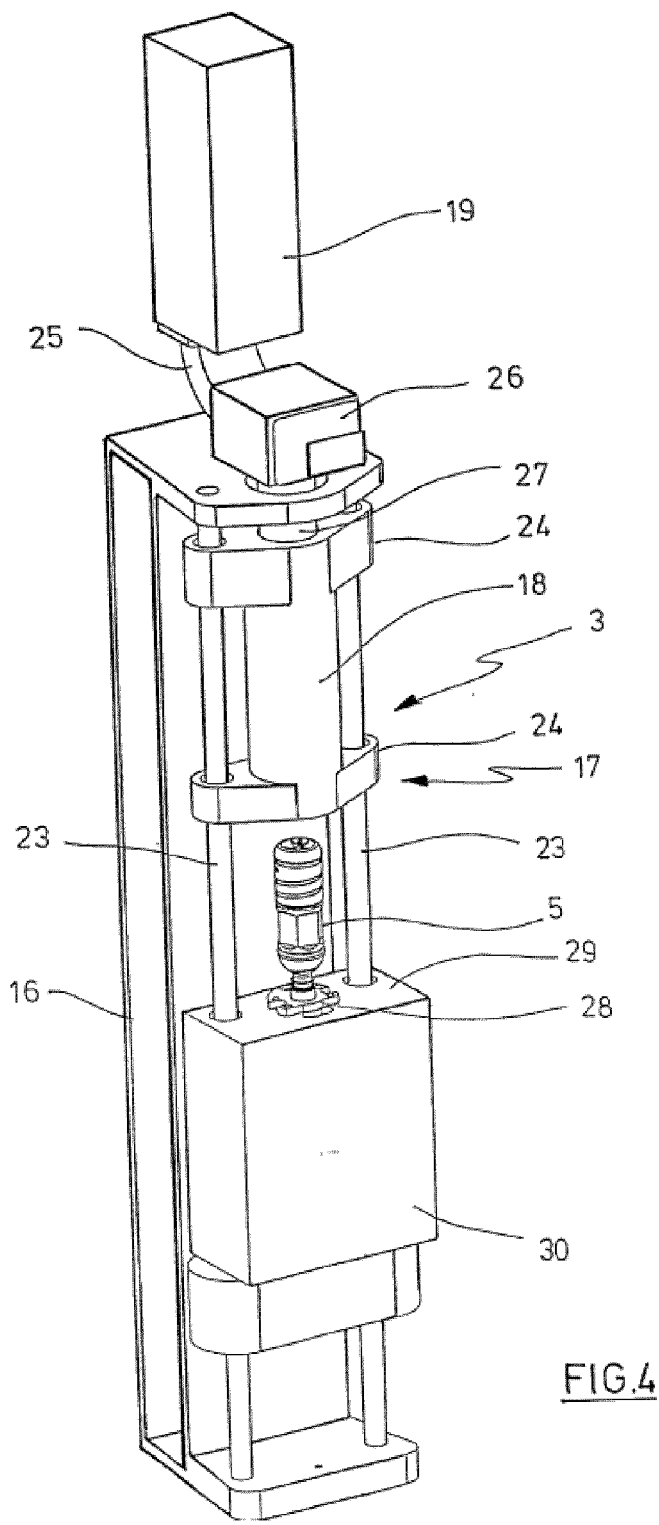

FIG. 4 shows a plasma station 3 in a perspective representation. It can be seen that the station frame 16 is provided with guide rods 23, on which a carriage 24 for holding the cylindrical chamber wall 18 is guided. FIG. 4 shows the carriage 24 with chamber wall 18 in a raised state, with the result that the container 5 is released.

The microwave generator 19 is arranged in the upper area of the plasma station 3. The microwave generator 19 is connected, via an elbow 25 and an adapter 26, to a coupling channel 27 which opens into the plasma chamber 17. In principle, the microwave generator 19 can be arranged both directly in the area of the chamber cover 31 and, via a spacer element coupled to the chamber cover 31, at a predefinable distance from the chamber cover 31, and thus in a larger surrounding area of the chamber cover 31. The adapter 26 has the function of a transition element and the coupling channel 27 is formed as a coaxial conductor. A quartz glass window is arranged in the area of an opening of the coupling channel 27 into the chamber cover 31. The elbow 25 is formed as a wave guide.

The container 5 is positioned by a holding element 28 which is arranged in the area of a chamber base 29. The chamber base 29 is formed as part of a chamber pedestal 30. To make adjustment easier, it is possible to fix the chamber pedestal 30 in the area of the guide rods 23. Another variant consists in securing the chamber pedestal 30 directly on the station frame 16. In the case of such an arrangement it is also possible, for example, to design the guide rods 23 in two parts in the vertical direction.

FIG. 5 shows a front view of the plasma station 3 according to FIG. 3 in a closed state of the plasma chamber 17. The carriage 24 with the cylindrical chamber wall 18 here is lowered compared with the positioning in FIG. 4, with the result that the chamber wall 18 has moved towards the chamber base 29. The plasma coating can be carried out in this positioning state.

FIG. 6 shows the arrangement according to FIG. 5 in a vertical sectional representation. It can be seen in particular that the coupling channel 27 opens into a chamber cover 31 which has a laterally protruding flange 32. In the area of the flange 32, a seal 33 is arranged which is impinged upon by an internal flange 34 of the chamber wall 18. In a lowered state of the chamber wall 18, a sealing of the chamber wall 18 with respect to the chamber cover 31 is hereby effected. A further seal 35 is arranged in a lower area of the chamber wall 18, in order to guarantee a sealing with respect to the chamber base 29 here as well.

In the positioning represented in FIG. 6 the chamber wall 18 surrounds the cavity 4, with the result that both an interior of the cavity 4 and a container interior 5.1 of the container 5 can be evacuated. To support a feed-in of process gas, in the area of the chamber pedestal 30 a hollow gas lance 36 is arranged which can be moved into the container interior 5.1 of the container 5. To carry out a positioning of the gas lance 36, the latter is held by a lance carriage 37, which is positionable along the guide rods 23. Inside the lance carriage 37, a process gas channel 38 runs which is coupled to a gas connection 39 of the chamber pedestal 30 in the raised positioning represented in FIG. 6. Through this arrangement, tubular connecting elements on the lance carriage 37 are avoided. In the state where the gas lance 36 has been moved into the container interior 5.1, the container interior 5.1 of the container 5 is isolated, i.e. sealed, with respect to the interior of the cavity 4. By contrast, in a lowered state of the gas lance 36 a gas-permeable connection between the container interior 5.1 of the container 5 and the interior of the cavity 4 is created.

Figure 7:
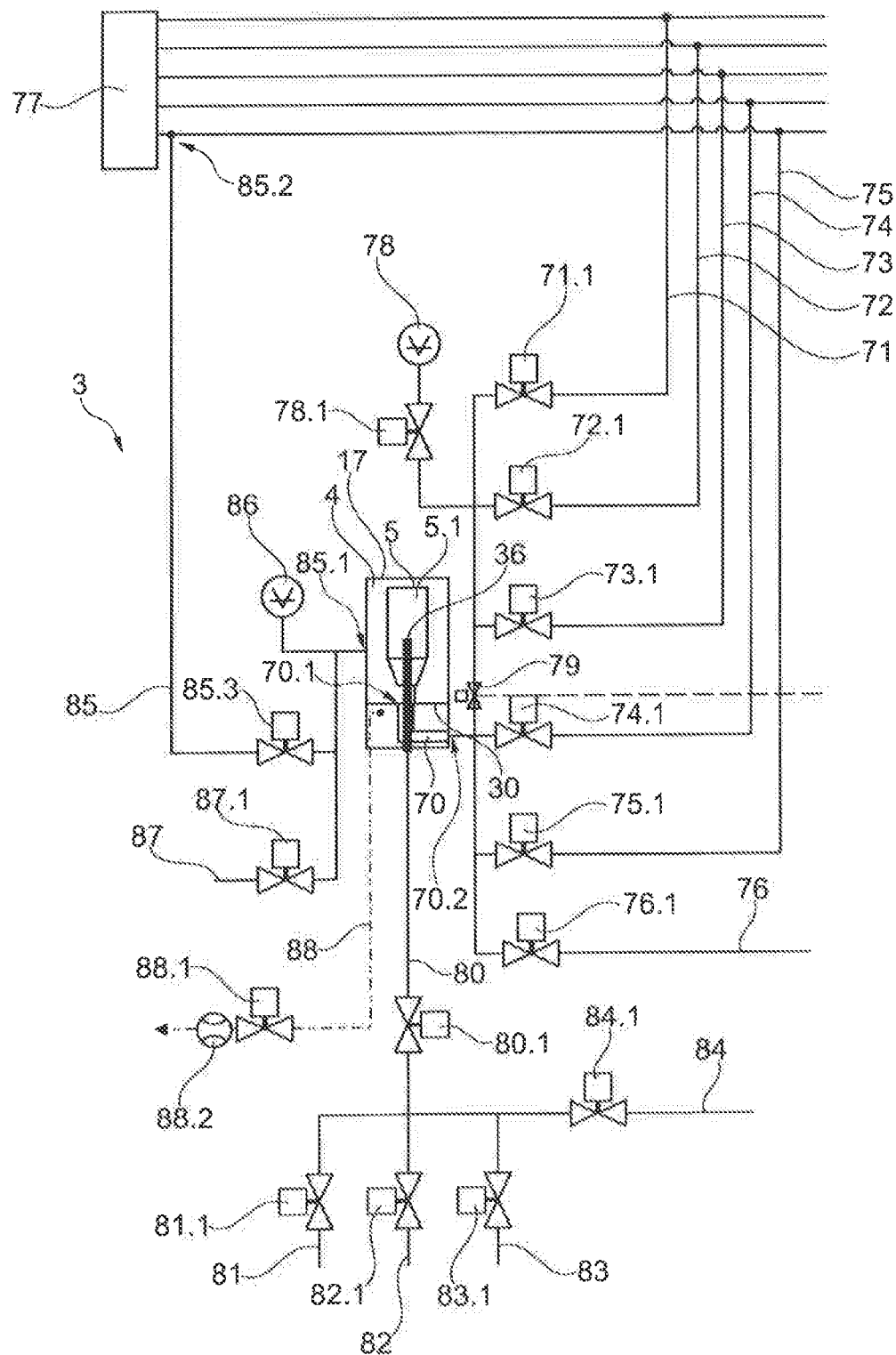

FIG. 7 shows, by way of example, a schematic block diagram using the example of a plasma station 3 of the plasma module 1. The plasma module 3 comprises at least the plasma chamber 17, into the interior of the cavity 4 of which the container 5 is inserted in a gas- and/or air-tight manner and positioned, as well as the chamber pedestal 30, which has at least one vacuum channel 70. The vacuum channel 70 opens with its first side 70.1 into the plasma chamber 17 or additionally also produces a gas-permeable connection into the container interior 5.1 of the container 5 depending on the position of the gas lance 36. In particular, it can be provided that in a state where the gas lance 36 has been moved into the container interior 5.1 the container interior 5.1 is isolated, i.e. sealed, with respect to the interior of the cavity 4, whereas in a lowered state of the gas lance 36 a gas-permeable connection between the container interior 5.1 of the container 5 and the interior of the cavity 4 is created.

Furthermore, at least one first to fifth vacuum line 71 . . . 75 as well as at least one first ventilation line 76 for a sterilization medium can be connected to a second side 70.2 of the vacuum channel 70, wherein in particular the first ventilation line 76 is formed so that it can be switched on and off via a regulatable and/or controllable valve device 76.1. In addition, each one of the first to fifth vacuum lines 71 . . . 75 can also in each case comprise at least one regulatable and/or controllable valve device 71.1 . . . 75.5, wherein the valve devices 71.1 . . . 76.1 are formed actuatable via a machine controller of the plasma module 1 not represented in more detail.

At the end facing away from the second side 70.2 of the vacuum channel 70, the first to fifth vacuum lines 71 . . . 75 are preferably in fluid-tight connection with a vacuum device 77 common to all the vacuum lines 71 . . . 75. The vacuum device 77 is set up in particular to generate the vacuum needed in the plasma chamber 17 as well as the container interior 5.1 during the plasma treatment. Furthermore, vacuum device 77 is set up to generate different negative pressures on the first to fifth vacuum lines 71 . . . 75, thus different negative pressure stages for each vacuum line 71 . . . 75. Alternatively, however, it is also possible to connect the individual vacuum lines 71 . . . 75 to separate vacuum devices 77 in each case.

In particular, it can be provided that the plasma chamber 17 and/or the container interior 5.1 are lowered to different negative pressure stages via the first to fifth vacuum lines 71 . . . 75. For example, it can be considered for this that the plasma chambers 17 including the container interior 5.1 are lowered to a first negative pressure stage via the first vacuum line 71 when the valve device 71.1 is opened, while a negative pressure stage lower than the first negative pressure stage is created both in the plasma chamber 17 and in the container interior 5.1 for example when the valve device 72.1 of the second vacuum line 72 is opened. Furthermore, it can also be provided that, for example, the fifth vacuum line 75 is formed as a process vacuum line which is set up to maintain the vacuum synchronously to supply a process gas during the plasma treatment. The process vacuum line provided thus prevents process gas evacuated by suction from passing over into the supply circuits of the further vacuum lines, for example the first to fourth vacuum lines 71 . . . 74.

The first to fifth vacuum lines 71 . . . 75 can also be assigned a pressure-measuring device 78 formed, for example, as a tube pressure gauge, which is set up to detect the negative pressure generated via the first to fifth vacuum lines 71 . . . 75. In particular, the pressure-measuring device 78 can be assigned an upstream valve device 78.1 and the pressure-measuring device 78 can be arranged in a fluid connection of the second vacuum line 72 to the second side 70.2 of the vacuum channel 70.

Furthermore, in a fluid connection between the third vacuum line 73 and the fourth vacuum line 74 with in each case the second side 70.2 of the vacuum channel 70, an additional blocking valve device 79 can preferably be provided, which is likewise formed regulatable and/or controllable and which is closed in particular during the ventilation of at least the container interior 5.1 with the sterilization medium, in order to prevent, i.e. block, a contamination of the supply circuits for example of at least the first to third vacuum lines 71 . . . 73 with sterilization medium. Furthermore, it can also be provided that a rinsing medium is introduced into the supply circuits via the blocking valve device 79 after completed ventilation of at least the container interior 5.1, and the supply circuits contaminated with sterilization medium can thereby be cleaned.

In addition, the gas lance 36 can be coupled, via a, for example, central process gas line 80, to for example a first to third process gas line 81 . . . 83, via which in each case different process gas compositions can be fed in particular to the container interior 5.1 by means of the gas lance 36. Each one of the first to third process gas lines 81 . . . 83 can furthermore each have at least one valve device 81.1 . . . 83.1 that can be regulated and/or controlled for example via the central machine controller of the plasma module 1. The central process gas line 80 can therefore also comprise such a controllable and/or regulatable valve device 80.1. Furthermore, a second ventilation line 84 for the sterilization medium, which is formed so that it can be switched on and off via a regulatable and/or controllable valve device 84.1 and by means of which at least the container interior 5.1 can be loaded with the sterilization medium, thus can be fed into it, can also be connected to the, for example, central process gas line 80. For example, the second ventilation line 84 can open in a fluid-tight manner into the central process gas line 80 in a fluid connection of the third process gas line 83.

Furthermore, a sixth vacuum line 85 with a first side 85.1 can also be connected directly and in particular in a fluid-tight manner to the plasma chamber 17, or can open into the latter, and with a second side 85.2 can interact in a fluid-tight manner with the central vacuum device 77, with interconnection of a regulatable and/or controllable valve device 85.3 via the fifth vacuum line 75. The sixth vacuum line 85 can also be assigned a pressure-measuring device 86 formed, for example, as a tube pressure gauge for measuring in particular the negative pressure inside the plasma chamber 17. Finally, for loading the plasma chamber 17 or the interior of the cavity 4 with the sterilization medium, a third ventilation line 87, which branches off from the sixth vacuum line 85 in a fluid-tight manner and is formed so that it can be switched on and off via a regulatable and/or controllable valve device 87.1 assigned to it, can preferably be provided between the first side 85.1 of the sixth vacuum line 85 and its valve device 85.3. In other words, via the sixth vacuum line 85 it is thus possible both to generate a negative pressure in the interior of the cavity 4 and to introduce a sterilization medium via the branched-off third ventilation line 87.

To supply operating fluid, in particular the first, second and third ventilation lines 76, 84, 87 can interact with the ring line 21 of the rotary distributor 20 represented in FIG. 2, or can be connected thereto. The ends of the first, second and third ventilation lines 76, 84, 87 facing away from the plasma chamber 17 can interact with a sterilization device, not represented in more detail, common to all three ventilation lines 76, 84, 87 or also separate in each case. The sterilization device can be formed to produce or manufacture the sterilization medium, or as a receiving tank or as a preparation station for the sterilization medium. At least the first, second and third ventilation lines 76, 84, 87 can be produced or manufactured in particular from a material which is formed resistant to a chemical attack or reaction with the sterilization medium, in particular H2O2 or O3.

Furthermore, a suction line 88 only schematically indicated and opening into the plasma chamber 17 can be provided in order to evacuate by suction any sterilization medium still residually present after completed loading of at least the container interior 5.1 with the sterilization medium and before a repeated plasma treatment of a further container 5 in the plasma chamber 17 in particular from the first to third as well as the central process gas lines 80 . . . 83. The suction line 88 can be assigned a regulatable and/or controllable valve device 88.1 as well as a volumetric flow meter 88.2. A suction flow can therefore be generated in the suction line 88 via a suction device not represented in more detail. In particular, the evacuation by suction can be effected via the suction line 88 when the container opening is raised or the lance carriage 37 is lowered. The special feature of this additional suction line 88 and the associated components is that they are not needed for the coating process and thus need not be suitable, in terms of design, for achieving high vacuum. As these only serve to evacuate residual sterilization medium by suction, for example the suction line 88 must be designed first and foremost with respect to corrosion resistance. For this the suction line 88 can be made, for example, of a plastic (e.g. Teflon), stainless steel or another material with an anti-corrosion coating. Through the provision of this additional suction line 88 contact between the central vacuum device 77, and the corresponding feed lines and components, and the sometimes very corrosive sterilization media is reduced or completely prevented. Furthermore, through the decoupling of the process steps, the process times for the central vacuum device 77 can be kept to an almost undiminished level.

A typical treatment process is explained below using the example of a coating process and it is carried out such that firstly the container 5 is transported to the plasma wheel 2 using the input wheel and that the container 5 is inserted into the plasma station 3 in a pushed-up state of the sleeve-like chamber wall 18. After completion of the insertion process, the chamber wall 18 is lowered into its sealed positioning and firstly an evacuation of both the cavity 4 and the container interior 5.1 of the container 5 is carried out at the same time.

After the interior of the cavity 4 has been evacuated sufficiently, the gas lance 36 is moved into the container interior 5.1 of the container 5 and a sealing of the container interior 5.1 with respect to the interior of the cavity 4 is carried out by a shifting of the seal element 28. Equally possibly, the gas lance 36 can already be moved into the container 5 synchronously with the start of the evacuation of the interior of the cavity 4. The pressure in the container interior 5.1 can then be lowered even further. In addition, it is also considered to carry out the positioning movement of the gas lance 36 at least partially already in parallel with the positioning of the chamber wall 18. Once a sufficiently low negative pressure has been achieved, process gas is introduced into the container interior 5.1 of the container 5 and the plasma is ignited with the aid of the microwave generator 19. It can be provided in particular that, with the aid of the plasma, both an adhesion promoter and the actual barrier layer made of silicon oxides are deposited on an internal surface of the container 5.

After completion of the coating process, i.e. the plasma treatment, the gas lance 36 is again removed from the container interior 5.1, i.e. lowered, and at least the container interior 5.1 of the container 5 as well as optionally the plasma chamber 17 are at least partially ventilated with a sterilization medium, i.e. loaded with the sterilization medium, synchronously with or before the lowering of the gas lance 36. The sterilization medium can thus be introduced via the ventilation of the container interior 5.1 of the container 5 as well as optionally the plasma chamber 17. The ventilation of at least the container interior 5.1 with the sterilization medium takes place in particular still at a plasma station 3 of the plasma module 1, particularly preferably when this plasma station 3 is located in the area of the output wheel 12, but without having reached the latter.

Suitable in particular as sterilization medium is a sterilization medium containing hydrogen peroxide (H2O2) and/or ozone (O3), which is used for example together with hot sterile air and thus condenses on the colder container interior 5.1 for example as H2O2 condensate film. The sterilization medium can be present in particular in a state of aggregation in the form of gas, vapour or mist.

It can also be provided that the sterilization medium introduced into the container interior 5.1 in this way is subsequently activated and/or dried by introducing, for example, hot activation medium in the form of gas or vapour into the container interior 5.1 such that oxygen free radicals, which react with germs and contaminations present to sterilize the container 5, form due to a decomposition of H2O2. For example, the activation medium can be formed as sterile hot air with a temperature of from 130° C. to 150° C.

The activation and/or drying of the container interior 5.1 can be effected, for example, on the output wheel 12. Alternatively, the activation and/or drying of the respective container 5 can also be effected during the transport of the container 5 loaded with sterilization medium to the subsequent container-treatment machine, for example a filling machine. It can additionally be provided here that at least the area of the output wheel 12 of the plasma module 1 is encased such that a sterile environment is ensured. For example, the encasing provided can be carried out with sterile air. In addition, the transport section to the subsequent container-treatment machines can also be formed encased and/or the containers 5 loaded with sterilization medium can be activated and/or dried on or during the transport to the subsequent container-treatment machine. Such sterile encasings are known to a person skilled in the art and therefore do not require more detailed explanation.

A positioning of the chamber wall 18, of the seal element 28 and/or of the gas lance 36 can be effected using different drive assemblies. In principle, the use of pneumatic drives and/or electric drives, in one embodiment in particular as a linear motor, is conceivable. In particular, however, it is considered to realize a cam control to support an exact movement coordination with a rotation of the plasma wheel 2. The cam control can be designed, for example, such that cams, along which cam rollers are guided, are arranged along a circumference of the plasma wheel 2. The cam rollers are coupled to the components to be positioned in each case.

Firstly, after the plasma chamber 17 has been closed, for example the first and sixth valve devices 71.1 and 85.1 respectively are opened and thus both the container interior 5.1 and the interior of the plasma chamber 17 are evacuated via the first and sixth vacuum lines 71 and 85 respectively. This occurs in the case of an additionally opened valve device 79.1 of the blocking line 79. During this the valve device 80.1 of the central process gas line 80 as well as the valve device 88.1 of the suction line 88 are preferably closed. In particular, during the evacuation of the container interior 5.1 as well as of the plasma chamber 17 the corresponding valve devices 76.1, 84.1 and 87.1 of the first to third ventilation lines 76, 84, 87 are also closed. After the first valve device 71.1 has been closed, for example the second valve device 72.1 can be opened and thus the container interior 5.1 can be lowered via the second vacuum line 72 to a lower pressure level. The container interior 5.1 and/or the plasma chamber 17 can also still be lowered via the third or fourth vacuum line 73, 74 to even lower negative pressure stages, if necessary. After a sufficiently low pressure level has been reached in the container interior 5.1 and/or the plasma chamber 17, the corresponding valve devices 71.1 . . . 75.1 can be closed. Alternatively, it can also be provided that, to provide a further sufficiently low pressure level in the container interior 5.1 and the plasma chamber 17 during the subsequent treatment steps, in particular the fifth valve device 75.1 as well as the sixth valve device 85.1 remain opened.

At the same time as or before a positioning of the gas lance 36 inside the container interior 5.1, one or more of the first to third valve devices 81.1 . . . 83.1 of the first to third process gas lines 81 . . . 83 as well as the valve device 80.1 of the central process gas line 80 can already be opened and a process gas with a particular composition can in particular be fed to the container interior 5.1 via the gas lance 36. Before or at the same time as this, the valve device 79.1 of the blocking line 79 is closed.

After sufficient process gas has been fed in, the microwave generator 19 ignites the plasma in the container interior 5.1 of the container 5. In this connection, it can be provided that, for example, the valve device 81.1 of the first process gas line 81 closes at a predefinable point in time, while the valve device 82.1 of the second process gas line 82 is opened to feed in a process gas with a second composition. At least occasionally, the fifth valve device 76.1 and/or the sixth valve device 85.3 can also be opened, in order to maintain a sufficiently low negative pressure in particular in the container interior 5.1 and/or the process chamber 17. Here, a pressure level of approx. 0.3 mbar has proved to be expedient.

After completion of the plasma treatment, the valve devices 81.1 . . . 83.1 of the first to third process gas lines 81 . . . 83 as well as all of the valve devices 71.1 . . . 75.1, 85.3 of the first to sixth vacuum lines 71 . . . 75, 85 still opened at this point in time are closed, while at least the valve device 84.1 of the second ventilation line 84 is opened and at least the container interior 5.1 of the container 5 is at least partially ventilated, i.e. loaded, with a sterilization medium after the plasma treatment at the plasma station 3. The sterilization medium is preferably introduced into the container interior 5.1 via the gas lance 36. Synchronously with this, the gas lance 36 can be lowered out of the container interior 5.1 and/or the valve device 76.1 of the second ventilation line 76 can be opened, in order thus at least partially to ventilate, i.e. load, at least the container interior 5.1 of the container 5 with a sterilization medium after the plasma treatment at the plasma station 3. Furthermore, a ventilation or loading of the plasma chamber 17 or of the container external wall of the container 5 with sterilization medium can thus also be effected. Furthermore, the ventilation of the plasma chamber 17 or of the container external wall of the container 5 with sterilization medium can also be effected by subsequently opening the valve device 87.1 of the third ventilation line 87.

After a sufficient loading or ventilation of the container interior 5.1 and the plasma chamber 17 with the sterilization medium, preferably up to at least atmospheric pressure or ambient pressure, the opened valve devices 76.1, 84.1, 87.1 of the first to third ventilation lines 76, 84, 87 are closed. The ventilation time per container 5 is between 0.1 and 0.4 seconds, preferably approximately 0.2 seconds. Furthermore, the residence time of the respective container 5 loaded with sterilization medium after the ventilation is still approximately 2.5 seconds on the plasma module 1, until the corresponding container 5 is delivered to a further transport section via the output wheel 12.

Subsequently, a rinsing and/or evacuation by suction of the residual sterilization medium, via for example, the fourth and/or fifth vacuum line 74, 75 and/or the suction line 88 can be effected in order to eliminate the sterilization medium still present in the first to third as well as the central process gas lines 80 . . . 83 and the plasma chamber 17 after the ventilation. Furthermore, it can also be provided that a rinsing medium is introduced into the supply circuits via the blocking valve device 79 after completed ventilation of at least the container interior 5.1, and the supply circuits contaminated with sterilization medium can thereby be cleaned.

After ambient pressure has been reached inside the cavity 4, the chamber wall 18 is raised again. Subsequently, a removal or delivery of the coated container 5 loaded with sterilization medium is effected on the output wheel 12.

The invention has been described above using embodiment examples. It is understood that numerous alterations as well as modifications are possible without thereby departing from the inventive concept forming the basis of the invention.

| List of Reference Numbers | |
|---|---|
| 1 | plasma module |
| 2 | plasma wheel |
| 3 | plasma station |
| 4 | cavity |
| 5 | container |
| 5.1 | container interior |
| 6 | input |
| 7 | separating wheel |
| 8 | delivery wheel |
| 9 | supporting arm |
| 10 | pedestal |
| 11 | input wheel |
| 12 | output wheel |
| 13 | output section |
| 14 | supporting ring |
| 15 | machine pedestal |
| 16 | station frame |
| 17 | plasma chamber |
| 18 | chamber wall |
| 19 | microwave generator |
| 20 | rotary distributor |
| 21 | ring line |
| 23 | guide rod |
| 24 | carriage |
| 25 | elbow |
| 26 | adapter |
| 27 | coupling channel |
| 28 | holding element |
| 29 | chamber base |
| 30 | chamber pedestal |
| 31 | chamber cover |
| 32 | flange |
| 33 | seal |
| 34 | internal flange |
| 35 | seal |
| 36 | gas lance |
| 37 | lance carriage |
| 38 | process gas channel |
| 39 | gas connection |
| 70 | vacuum channel |
| 70.1 | first side |
| 70.2 | second side |
| 71 | first vacuum line |
| 71.1 | valve device |
| 72 | second vacuum line |
| 72.1 | valve device |
| 73 | third vacuum line |
| 73.1 | valve device |
| 74 | fourth vacuum line |
| 74.1 | valve device |
| 75 | fifth vacuum line |
| 75.1 | valve device |
| 76 | first ventilation line |
| 76.1 | valve device |
| 77 | vacuum device |
| 78 | pressure-measuring device |
| 78.1 | valve device |
| 79 | blocking valve device |
| 80 | central process gas line |
| 80.1 | valve device |
| 81 | first process gas line |
| 81.1 | valve device |
| 82 | second process gas line |
| 82.2 | valve device |
| 83 | third process gas line |
| 83.1 | valve device |
| 84 | second ventilation line |
| 84.1 | valve device |
| 85 | sixth vacuum line |
| 85.1 | first side |
| 85.2 | second side |
| 85.3 | valve device |
| 86 | pressure-measuring device |
| 87 | ventilation line |
| 87.1 | valve device |
| 88 | suction line |
| 88.1 | valve device |
| 88.2 | volumetric flow meter |

We claim:

1. An apparatus for plasma treatment of containers comprising:
at least one plasma station arranged on a plasma wheel, said at least one plasma station including at least one plasma chamber configured to receive a container having an interior;
at least one vacuum line connected to the at least one plasma chamber for at least partially evacuating the at least one plasma chamber and the interior of the container before a plasma treatment;
at least one controllable valve device provided in the at least one vacuum line;
at least one process gas line connected to the at least one plasma chamber for supplying a process gas for forming an internal coating on the interior of the container during the plasma treatment;
at least one controllable valve device provided in the at least one process gas line;
a first ventilation line connected to the at least one plasma chamber for supplying a sterilization medium in a form of the gas, vapor or mist to at least partially ventilate both the at least one plasma chamber and the interior of the container after the plasma treatment;

at least one controllable valve device provided in the first ventilation line; and a machine controller;

wherein the machine controller is configured to control the at least one at least one controllable valve device provided in the at least one vacuum line such that the at least one plasma chamber and the interior of the container is at least partially evacuated before the plasma treatment, wherein the machine controller is configured to control the at least one at least one controllable valve device provided in the at least one process gas line such that process gas is supplied for forming the internal coating on the interior of the container during the plasma treatment, and wherein the machine controller is configured to control the at least one controllable valve device provided in the first ventilation line such that the sterilization medium in the form of the gas, vapor or mist is supplied to at least partially ventilate both the at least one plasma chamber and the interior of the container after the plasma treatment.

2. The apparatus according to claim 1, wherein the at least one process gas line is connected to a central process gas line, wherein a second ventilation line is coupled in a fluid-tight manner to the central process gas line, and wherein at least one controllable valve device is provided in the second ventilation line.

3. The apparatus according to claim 1, wherein the first ventilation line is coupled in a fluid-tight manner to a vacuum channel.

4. The apparatus according to claim 3, wherein a third ventilation line is coupled in a fluid-tight manner to the at least one plasma chamber.

5. The apparatus according to claim 1, further comprising a suction line opening into the at least one plasma chamber.

6. The apparatus according to claim 1, further comprising an output wheel for transferring a plasma-treated container from the at least one plasma station.

7. The apparatus according to claim 6, wherein a sterile encasing is provided at least in an area of the output wheel.

8. The apparatus according to claim 1, wherein the at least one plasma station includes a gas lance in fluid communication with the first ventilation line, and wherein the gas lance is controlled so as to be selectively inserted into the interior of the container for at least partially ventilating the container interior and retracted from the interior of the container for at least partially ventilating the at least one plasma chamber after the plasma treatment.

9. The apparatus according to claim 1, wherein the at least one plasma station is configured to receive at least two containers at the same time.

\* \* \* \* \*